(12) United States Patent
Perrier et al.

(10) Patent No.: US 6,303,150 B1
(45) Date of Patent: Oct. 16, 2001

(54) METHOD FOR PRODUCING NANOCAPSULES WITH CROSSLINKED PROTEIN-BASED WALLS NANOCAPSULES THEREBY OBTAINED AND COSMETIC, PHARMACEUTICAL AND FOOD COMPOSITIONS USING SAME

(75) Inventors: Eric Jean-Luc Perrier, Vienne; Alain Roger Huc, Sainte Foy les Lyon, both of (FR)

(73) Assignee: Coletica, Lyons (FR)

(*) Notice: Subject to any disclaimer, the term of this patent is extended or adjusted under 35 U.S.C. 154(b) by 0 days.

(21) Appl. No.: 08/232,014

(22) PCT Filed: Oct. 27, 1992

(86) PCT No.: PCT/FR92/01003

§ 371 Date: May 2, 1994

§ 102(e) Date: May 2, 1994

(87) PCT Pub. No.: WO93/08908

PCT Pub. Date: May 13, 1993

(30) Foreign Application Priority Data

Oct. 31, 1991 (FR) .................................................. 91 13522

(51) Int. Cl.[7] ................................ A61K 9/16; A61K 9/50; A61K 7/00
(52) U.S. Cl. ......................... 424/491; 424/492; 424/401; 424/499; 424/493
(58) Field of Search .................................... 424/491, 492, 424/401, 499, 493; 514/938; 264/4.1, 4.3

(56) References Cited

U.S. PATENT DOCUMENTS

| | | | |
|---|---|---|---|
| 4,273,672 | * 6/1981 | Vassiliadis | 252/316 |
| 4,871,716 | * 10/1989 | Longo | 514/2 |
| 4,921,705 | * 5/1990 | Arai | 424/450 |
| 5,055,300 | * 10/1991 | Gupta | 424/409 |
| 5,069,936 | * 12/1991 | Yen | 424/213.3 |
| 5,395,620 | 3/1995 | Huc et al. | 424/499 |

FOREIGN PATENT DOCUMENTS

| | | |
|---|---|---|
| 495261 | 3/1977 | (AU) . |
| 89/01221 | 1/1989 | (FR) . |
| 2 642 329 | 8/1990 | (FR) . |

OTHER PUBLICATIONS

Reza Arshady, "Albumin Microspheres and Microcapsules: Methodology of Manufacturing Techniques," *Journal of Controlled Release*, 14 (1990) 111–131, Elsevier Science Publishers B.V., Amsterdam.

Zubay, *Biochemistry*, 3rd edition p. 149 1993.*

Verified English translation of French Patent 89/01221 dated Sep. 21, 1995.

* cited by examiner

*Primary Examiner*—Thurman K. Page
*Assistant Examiner*—A. Pulliam
(74) *Attorney, Agent, or Firm*—Millen, White, Zelano & Branigan, P.C.

(57) ABSTRACT

A method for producing nanocapsules with cross-linked protein-based walls, comprising preparing emulsions of said proteins and crosslinking these with a crosslinking agent having reactive groups which react with the reactive groups of said proteins, particularly acylatable groups, to cause an interfaced crosslinking reaction between the proteins and the crosslinking agent, and thereby form capsules with walls based on the proteins crosslinked by the crosslinking agent. A fine emulsion of said proteins is prepared by adjusting the surface tension of the various liquid phases. Biocompatible and biodegradable nanocapsules having improved controlled release are thereby obtained.

55 Claims, 2 Drawing Sheets

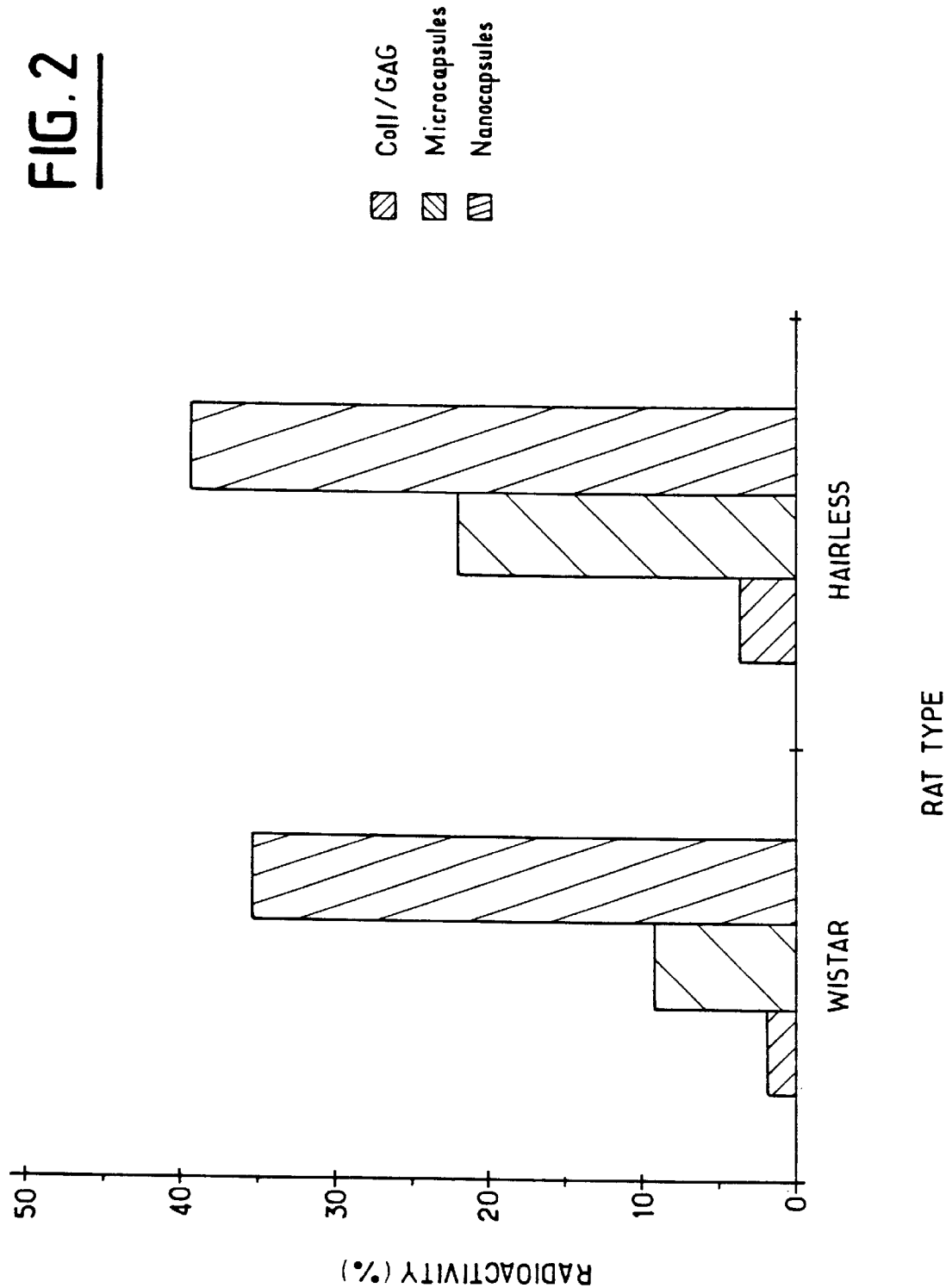

Figure 1:
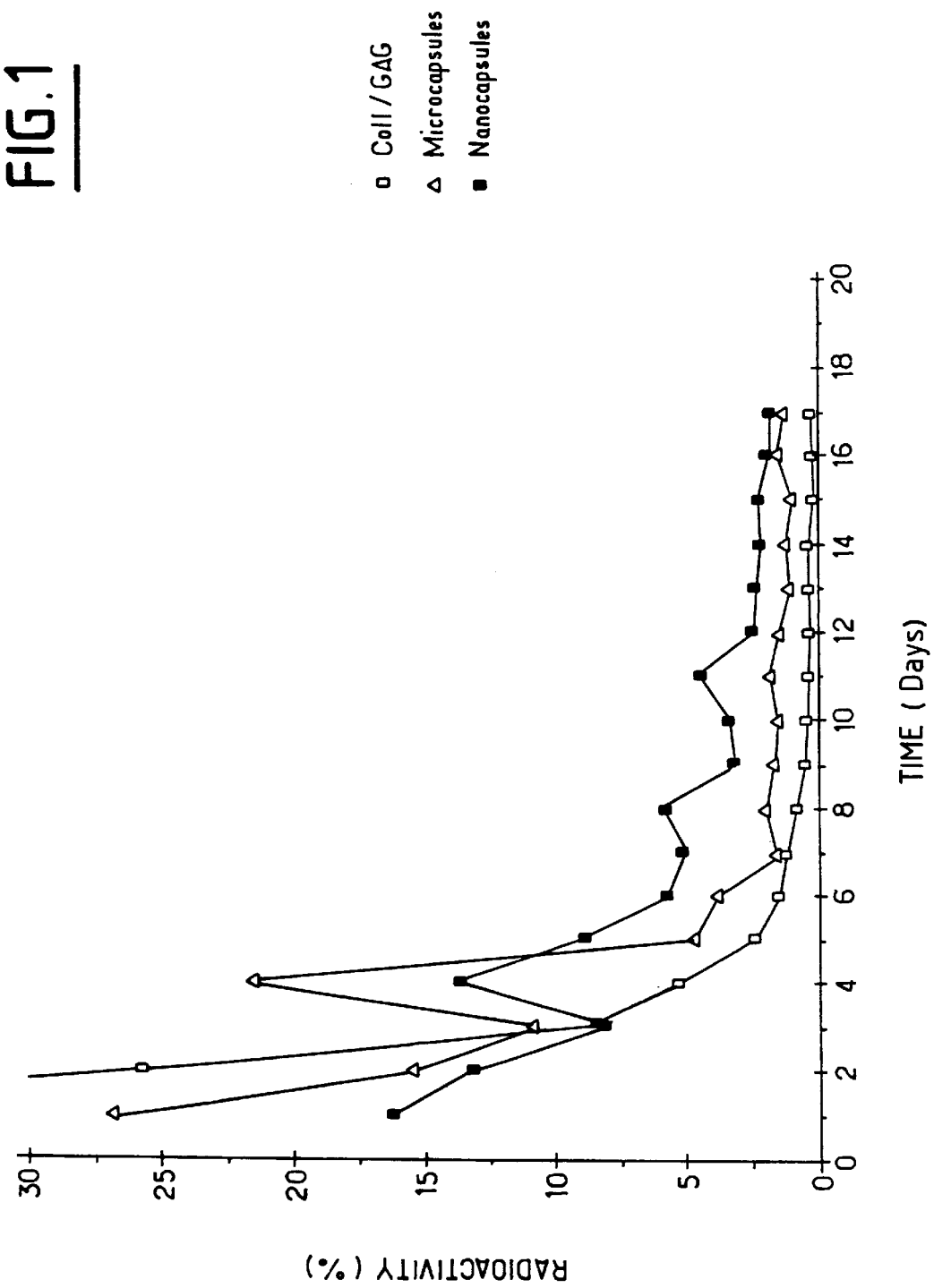

METHOD FOR PRODUCING NANOCAPSULES WITH CROSSLINKED PROTEIN-BASED WALLS NANOCAPSULES THEREBY OBTAINED AND COSMETIC, PHARMACEUTICAL AND FOOD COMPOSITIONS USING SAME

BACKGROUND OF THE INVENTION

The present invention relates essentially to a process for the production of nanocapsules with cross-linked protein-based walls, to the nanocapsules thereby obtained and to cosmetic, pharmaceutical or food compositions in which they are present.

It is known that the encapsulation of active substances is very important either for protecting the active principle or for permitting a slow or delayed release of the active principle in the organism.

It has been proposed to encapsulate the active principles in liposomes, the latter being an interesting galenical form view their very good affinity with the cell membranes, their very good biocompatibility and their submicron size.

However, these structures have numerous limitations, to see even major disadvantages, which can be summarized in the following four points:

A poor encapsulation yield: liposomes can contain or transport different types of molecules, namely hydrophilic, lipophilic and amphiphilic molecules. However, the encapsulation yields are very low in all cases, which, coupled with the problem of diffusion of the active principles, further reduces the efficacy of the liposomes and in many cases does not permit consideration of their use in therapeutic applications.

A poor reproducibility of the liposome preparations when they are to be produced on the industrial scale.

Instability in vitro: this can manifest itself in various ways, namely chemical instability of the lipids, instability of the size of the liposomes, instability of their structure, formation of aggregates, release of the encapsulated active principles, etc.

Instability in vivo: the influence of biological fluids on the liposomes very often increases their membrane permeabilities. Depending on the administration route used, the liposomes can be in contact with biological fluids as diverse as blood, digestive juices, interstitial fluids etc. and must consequently be capable of withstanding numerous interactions. Now, contact with the majority of biological fluids results in a marked increase in the membrane permeability of the liposomes. By imperfect fusion with the cells, or by contact with salts, enzymes—lipases, phospholipases, acyltransferases—plasma constituents, bile salts or digestive juices, or by simple pH variations, the liposomes can release their active principles into the surrounding medium almost instantaneously.

It has also been proposed to encapsulate the active principles in particles or capsules with dimensions of the order of a few microns. For example, in the document FR-A-2 642 329 identified also by application Ser. No. 89 01221, the same application which forms the basis of priority of U.S. Pat. No. 5,395,620, the Applicant has proposed the preparation of microcapsules with mixed atelo-collagen/glycosaminoglyan walls for encapsulation of the active principle. This method is totally satisfactory except that it does not make it possible to prepare capsules of submicron dimensions, i.e. capsules of nanometer dimensions, called nanoparticles.

Furthermore, nanocapsules with polyacrylamide walls have been proposed, especially by Couvreur et al. in Febs Letters (1977), 84, 323–326, and nanocapsules with polymethyl and polyethyl cyanoacrylate walls have been proposed by the same authors in J. Pharm. Pharmacol. (1979), 31, 331–332. Likewise, it has been proposed in EP-A-0 274 961 to prepare nanocapsules forming colloidal systems based on a vinyl chloride/vinyl acetate copolymer, polyisobutyl cyanoacrylate and poly-(d,l)-lactic acid; in U.S. Pat. No. 4,640,709, BEESTMAN et al. have proposed the preparation, by polycondensation, of small spheres whose membranes consist of a polymeric material such as polyurea, polyamide, polysulfonamide, polyester, polycarbonate and polyurethane.

However, although the latter documents afford capsules of nanometer dimensions, there is a major problem in the fact that these particles generally have poor biocompatibility and poor biodegradation in vitro and in vivo, which may result in the accumulation of a high concentration of particles in certain organs, the toxicity of certain monomers, certain polymerization by-products or certain degradation by-products, and poor protection of the active principles when they are only adsorbed on the surface of the nanoparticles, thereby giving an inadequate delaying effect.

SUMMARY OF THE INVENTION

One object of the present invention is thus to solve the new technical problem which consists in providing a solution making it possible to produce particles of nanometer dimensions, called nanoparticles, especially in the form of nanocapsules or nanospheres exhibiting good biocompatibility, good biodegradation in vivo and zero toxicity or a very low toxicity, together with very good protection of the active principles and a significant delaying effect.

A further object of the present invention is to solve the abovementioned new technical problem in a simple and inexpensive manner which can be used on the industrial scale.

The present invention makes it possible for the first time to solve these technical problems in a simple, inexpensive and reliable manner which can be used on the industrial scale and in the field of cosmetics, pharmacy or agri-foodstuffs, by the production of particles or capsules of submicron dimensions, i.e. with a size of less than 1 $\mu$m and especially of between about 100 and 800 nanometers.

Thus, according to a first feature, the present invention provides a process for the production of capsules of very small dimensions, called nanocapsules, with crosslinked protein-based walls, which comprises preparing a very fine emulsion of said proteins called a nanoemulsion, either of the water-in-oil type or of the oil-in-water type, and forming said nanocapsules from said nanoemulsion, wherein an interfacial crosslinking reaction is carried out, (without heating,) between said proteins and a crosslinking agent comprising reactive groups capable of reacting with the reactive groups of said proteins, particularly acylatable groups, so as to produce said nanocapsules with crosslinked protein-based walls.

In one variant of this process, the viscosity difference between the liquid phases present is reduced by the addition of a viscosity modifier to one of the two phases.

In another variant of this process, the viscosity modifier is capable of modifying the viscosity by a factor of at least 4 and preferably at least 10, relative to the phase to which said modifier is added.

In another variant of this process, in the case of the formation of a water-in-oil emulsion, said viscosity modifier is added to or substituted for the oily phase so as to increase the viscosity by a factor of at least 4, relative to the viscosity of the oily phase conventionally used.

In another variant of this process, in the case of an oil-in-water emulsion, the viscosity of the aqueous phase is reduced either by reducing the proportion of protein or by adding a viscosity modifier to the aqueous phase (viscosity reducer) so as to reduce its viscosity, and preferably by a factor of at least 4, relative to the viscosity of the aqueous phase conventionally used.

In another variant of this process, the protein used is a protein with a film-forming effect which is preferably selected from the group consisting of an animal protein such as elastin, keratin, silk, albumin, milk proteins or structural proteins such as collagen, especially collagen without telopeptide, or atelocollagen a vegetable protein such as wheat, maize, oat or almond protein; and a protein originating from the marine environment, extracted especially from fish, algae or else plankton or micro-plankton.

In another variant of this process, the above-mentioned protein has a molecular weight of at least 50,000 Daltons, this protein being used by itself or in a mixture.

In another variant of this process, the proportion of protein in the emulsion solution varies between 0.1 and 5% by weight, based on the total weight of the emulsion.

In another variant of this process, the protein is initially dissolved in a buffered aqueous solution whose pH is slightly basic, preferably between about 7.5 and about 10.5.

In another variant of this process, the above-mentioned viscosity modifier is a viscous oil selected in particular from viscous liquid paraffin whose viscosity is preferably at least 80 cp and particularly preferably at least 200 cp, or a viscosity modifier for oils such as magnesium stearate.

In another variant of this process, a surfactant or emulsifying agent capable of forming a nanoemulsion, preferably glycerol sorbitan hydroxyisostearate, is used in the emulsion step.

In another variant of this process, the emulsion step is carried out by means of stirring with a shear effect, preferably at a minimum of 20,000 rpm, or with a cavitation effect.

In another variant of this process, a very fine emulsion is produced by passing the emulsion through a homogenizer under a pressure of at least 400 bar, this homogenizer preferably being a French press.

In another variant of this process, the above-mentioned protein comprises collagen.

In another variant of this process, the above-mentioned protein comprises atelocollagen.

In another variant of this process, the above-mentioned protein comprises a mixture of atelocollagen and glycosaminoglycan.

In another variant of this process, one of the phases contains a water-soluble, liposoluble or insoluble active principle for use in cosmetics, pharmaceuticals or foodstuffs.

In yet another variant, when a water-soluble active substance is employed, an oil/water emulsification ratio of about 6 is used.

In another variant, when a liposoluble active principle is employed, a protein with a high or very high molecular weight, i.e. of at least 50,000 Daltons, is used at a concentration such that the viscosity of the solution obtained is low, i.e. below 20 cp.

It is also preferable to use a water/oil emulsification ratio of about 20 in this case.

Furthermore, any crosslinking agent well known to those skilled in the art, as described especially in FR-A-2 642 329, is employed within the framework of the process. This cross-linking agent is dissolved in the oily phase and is an acid dichloride, an acid anhydride or a dibasic or polybasic carboxylic acid. According to a preferred characteristic, the crosslinking agent is selected from terephthaloyl chloride, phthaloyl chloride, sebacoyl chloride, succinoyl chloride, the chloride of a tricarboxylic acid such as citric acid, or an acid anhydride such as succinic anhydride.

According to a second feature, the present invention also covers capsules of very small dimensions, called nanocapsules, which comprise crosslinked protein walls and are preferably prepared by the process as defined above.

Then, represented according to a third feature, the present invention also covers a cosmetic, pharmaceutical or food composition which comprises nanocapsules with crosslinked protein-based walls, preferably obtained by the process defined above. Preferably, these nanocapsules at least partially contain an active principle, in particular a water-soluble, liposoluble or insoluble active principle for use in cosmetics, pharmaceuticals or foodstuffs.

Other objects, characteristics and advantages of the invention will become clearly apparent from the following explanatory description referring to various Examples of the invention, which are given simply by way of illustration and cannot therefore in any way limit the scope of the invention. Unless indicated otherwise, all the percentages are given by weight in the Examples.

EXAMPLE 1 ACCORDING TO THE INVENTION

Preparation of nanocapsules with protein walls based on an atelocollagen/glycosaminoglycan mixture a) Production of the Mixture Required to Produce the Nanocapsules This mixture is prepared by a procedure described in FR-A-2 642 329, Example 1, steps a) to c).

The collagen is extracted from hides of freshly slaughtered calves and the telopeptides are then removed to give atelocollagen.

The chondroitin 4-sulfate is extracted from calves' nasal septa, dialyzed and then lyophilized.

The above two preparations are advantageously placed in a basic buffer such as carbonate or phosphate or any other substance affording a buffer capacity between 7.5 and 10.5. The solutions are then mixed to give for example the following final concentrations:

| | |
|---|---|
| Atelocollagen: | 1.6% |
| Chondroitin 4-sulfate: | 0.6% |
| Anhydrous sodium carbonate: | 4.8% |
| Methyl parahydroxybenzoate: | 0.4% |
| Softened water: | qsp |

The pH of the whole is brought to between 7.5 and 10.5, for example to 8.5, by the addition of 6 N HCl or 6 N NaOH.

One kilogram of the solution prepared in this way is used in the subsequent production.

b) Preparation of the Crosslinking Agent 400 g of terephthaloyl chloride are ground in a mortar and added to 1 l of CODEX viscous liquid paraffin. The whole is stirred mechanically.

c) Emulsification 6 l of CODEX viscous liquid paraffin of viscosity index 250 cp and preferably 320 ml of a surfactant, for example glycerol sorbitan hydroxyisostearate (Arlacel 780, ICI), are introduced into a cooled stainless steel vessel. The whole is stirred for a few minutes.

The already prepared solution of atelocollagen and chondroitin sulfate is then added and emulsification is performed in a few minutes at 20,000 rpm using an Ultra-Turax®.

d) Crosslinking

The solution containing the crosslinking agent prepared in step b is then introduced into the emulsion. The solid particles present therein are also added and will dissolve over time.

After stirring for 5 min. at 20,000 rpm with the Ultra-Turax®, the solution is stirred mechanically at a reduced speed of rotation for at least 18 h.

The nanocapsules are separated off by batch centrifugation and the supernatant is removed (4000 rpm for 15 min.).

e) Washes

The nanocapsules are washed with five successive solutions of an organic phase miscible with liquid paraffin. Examples which may be mentioned are DRAGOXAT® (DRAGOCO), ISOPROPYL MYRISTATE (STEARINIERIE DUBOIS), triglycerides (STEARINERIE DUBOIS), etc.

In the course of each wash, 100 ml of nanocapsules are added to 500 ml of organic phase. The whole is stirred for a few minutes and then centrifuged (4000 rpm for 15 min.).

The nanocapsules obtained can be suspended for example in protein or polysaccharide gels or in an oily phase.

EXAMPLE 2 OF THE INVENTION

Preparation of nanocapsules containing a water-soluble or insoluble active principle The procedure is the same as described in Example 1, except that numerous active principles can be added to the solution produced in a), examples being:

Ex. 2A: 64 g of GLYCENTANE® (Bioética)
Ex. 2B: 64 g of GINKGO BILOBA (Alban Muller Int.)
Ex. 2C: 32 g of GLUCOSE (MERCK)
Ex. 2D: 32 g of an amino acid such as L-glutamine
Ex. 2E: 32 g of CAFFEINE (SIGMA).

EXAMPLE 3 OF THE INVENTION

Preparation of nanocapsules with atelocollagen-based protein walls

The procedure is the same as described in Example 1, except that atelocollagen at a concentration of 2% is used as the only macromolecular protein.

EXAMPLE 4 OF THE INVENTION

Elastin nanocapsules

The procedure is the same as described in Example 1, except that elastin is used as the protein.

It is also possible to choose a protein from animal proteins such as elastin, keratin, silk, albumin and milk proteins, vegetable proteins such as wheat, maize, oat and almond proteins, or proteins originating from the marine environment, such as collagen or other proteins extracted from fish, proteins from algae and microplankton.

EXAMPLE 5 OF THE INVENTION

All the Examples described above can be modified by using different methods of emulsification.

Thus, in Example 1 in particular, the emulsification step c) is modified and, after gentle mixing by mechanical stirring, the whole is passed one or more times through a high-pressure homogenizer.

The pressures used can be between 400 and 1000 bar, but are preferably around 700 bar. Either single-action or double-action homogenizers can be used, but single-action homogenizers will be preferred for very film-forming proteins.

Examples of high-pressure homogenizers which have been used are the Lab 60 (APV), the SHL 05 (ALPHA-LAVAL) or the SODEXIM 2720 or 2735 (SODEXIM). After a homogenization treatment at 700 bar for example, nanocapsules with dimensions of less than 1 $\mu$m, namely between 200 and 800 nanometers, are obtained.

Likewise, other apparatuses based on different principles can also enable high cavitation forces to be obtained. Such forces then make it possible to obtain nanoemulsions (examples: SONICATEUR® BRANDSON, SONOLATOR® from SONIC Corp.).

EXAMPLE 6 OF THE INVENTION

In the emulsification step of Example 1, an oil viscosity modifier is used to increase the viscosity of the emulsification solution, for example magnesium stearate in a proportion of 2% by weight. This gives nanocapsules with dimensions of between 200 and 800 nanometers.

EXAMPLE 7

Preparation of nanocapsules containing liposoluble active principles a) 750 ml of demineralized water are added to 250 ml of the solution described in Example 1a).
b) 5 ml of sebacoyl dichloride are added to 25 ml of borage oil and the whole is mixed by mechanical stirring.
c) The solutions a) and b) are combined continuously and sent into a high-pressure homogenizer of the Lab 60 type (APV). The homogenization pressures used are between 300 and 1000 bar, for example 800 bar, and several successive homogenizations were carried out with single-action and double-action valves. The spheres obtained have a size of less than one micron, are remarkably stable and, on account of their small size, do not settle out in a dilute storage medium.

EXAMPLE 8

Other liposoluble active principles

In Example 7, the 25 ml of borage oil can be replaced with:

Ex. 8a: 25 ml of ethyl myristate
Ex. 8b: 25 ml of isopropyl myristate
Ex. 8c: 25 ml of low-viscosity liquid paraffin
Ex. 8d: 25 ml of ethyl oleate
Ex. 8e: 25 ml of vitamin E acetate
Ex. 8f: 25 ml of benzyl benzoate

EXAMPLE 9

Objectivation test

Release in vivo of a substance encapsulated in nanocapsules according to the invention compared with microcapsules The most convincing objectivation test results provided by the nanocapsules are undeniably those associated with modification of the space-time distribution of the active substance. This modification can be related to the size of the particles, which are then transported specifically to certain parts of the organism (reticuloendothelial system, hepatic tissues), but it can also be related to the possible role of the nanocapsules as an active principle reservoir. In the latter case, a delayed release of the active principle can make it possible to achieve a high bioavailability of the active principle, a more intense assimilation and a much more gradual elimination of the waste products derived from the metabolization of the active principle.

The comparative study described below enabled the inventors to evaluate the presence and intensity of the delaying effect obtained with micrometer-size capsules and with nanometer-size capsules according to the invention.

a) Equipment and Methods

The dorsal skin of rats (male WISTAR, about 300 g) was treated with a water-in-oil emulsion, the oily phase being codex viscous liquid paraffin with a viscosity index of about 250 cp (TISCCO) and the aqueous phase being represented by one or other of the following solutions:

a collagen/glycosaminoglycan mixture (abbreviated to Coll/ GAG) containing radioactive paraaminobenzoic acid (PABA*);

type A microcapsules containing PABA* (mean size 50 $\mu$m), as prepared by the method described in Example 1 of patent FR-A-2 642 329; or nanocapsules containing PABA* (size between 100 and 800 nm), prepared by the method of Example 1 above.

After application of the test product to a constant area, the release of the acid was monitored by measurement of the radioactivity contained in the urine collected daily from each animal.

For each of the three solutions described above, two rats were treated with 0.3 g of emulsion having a specific radioactivity of about $3 \cdot 10^6$ cpm/g in the case of the collagen/GAG solution and the microcapsules, and of about $6 \cdot 10^5$ cpm/g in the case of the nanocapsules of the invention.

b) Results

After application of the encapsulated or non-encapsulated radioactive compound, the radioactivity was measured every day in the rats' urine. The curves showing the change in this radioactivity as a function of time (in days) are represented in FIG. 1.

The values plotted on this graph represent the radioactivity measured in the urine divided by the total radioactivity recovered from the urine and the skin. This total recovered radioactivity is assessed after the 17 days of measurements and after the animals have been sacrificed.

This graph describes the delaying effect observed with the microcapsules and the nanocapsules on the release of the PABA*. The high release found in the first few days with the solution of collagen/GAG is less intense with the microcapsules and very low with the nanocapsules. The PABA* is eliminated much more slowly when it is encapsulated in the microcapsules and even less quickly when it is encapsulated in the nanocapsules.

17 days after the treatment, the rats are sacrificed, the skin which received the application is hydrolyzed and then the radioactivity is measured. The results obtained have been collated in FIG. 2 and show that the radioactivity contained in the skin tissues is weak (about 4%) when the PABA* has not been encapsulated, much stronger (about 10%) when microcapsules have been used, and even more intense (>20%) when the radioactive substance has been encapsulated in nanocapsules.

This very distinct difference was confirmed in another experiment of the same type using male nude rats weighing 300 g.

c) Conclusions

The rate of elimination of the radioactivity found in the urine is directly related to the rate of skin absorption, so any delay in the elimination can be considered to be due to the delaying effect of the spheres encapsulating the radioactive element. This delaying effect found in vivo on rats is very marked with 50 $\mu$m microcapsules, but is even more intense with nanocapsules (whose size varies between 800 nm and 100 nm).

The radioactivity measured in the skin tissue after application of an encapsulated or non-encapsulated radioactive element is a measure of the bioavailability of this element, i.e. its capacity to be integrated into the skin's metabolism. After the application of an excessive amount of PABA*, the elimination is very rapid since the skin tissues can only accept an aliquot of the product applied.

When microcapsules or nanocapsules are used, there is a delayed release of PABA*, which can then be metabolized in greater amounts in the skin tissues.

This is what is observed with the nanocapsules of the invention and to a lesser degree with the micro-capsules.

If the capsules are sufficiently small not to burst when applied (diameter less than 100 $\mu$m), it is therefore possible to improve the bioavailability of the cosmetic active principles by using nanocapsules.

The present invention covers all means which constitute technical equivalents of the means described. In particular, in the description and the claims, the word "nanocapsule" is not restricted to actual capsules, but covers spheres or particles of nanometer dimensions.

What is claimed is:

1. A process for the production of nanocapsules or nanoparticles, said nanocapsules or nanoparticles having a size less than 1 micron, said nanocapsules or nanoparticles having crosslinked protein-based walls, which process comprises preparing a nanoemulsion of at least one acylatable group-containing protein, said emulsion comprising a water phase, an oil phase, defining an interface between said water phase and said oil phase either of a water-in-oil emulsion or an oil-in-water emulsion, and forming said nanocapsules or nanoparticles from said nanoemulsion, wherein an interfacial crosslinking reaction is carried out, between said protein and a crosslinking agent having reactive groups capable of reacting at said interface with said acylatable groups of said protein, so as to yield said nanocapsules or nanoparticles with crosslinked protein-based walls.

2. A process according to claim 1, an oil-in-water emulsion is prepared and the viscosity of the aqueous phase is reduced by a factor of at least 4, either by reducing the protein content or by adding a viscosity modifier.

3. A process according to claim 1, wherein the protein used is a protein with a film-forming effect selected from the group consisting of an animal protein, a vegetable protein and a protein originating from a marine source.

4. A process according to claim 3, wherein the said protein has a molecular weight of at least 50,000 Daltons.

5. A process according to claim 1, wherein the proportion of protein in the emulsion solution varies between 0.1 and 5% by weight, based on the total weight of the emulsion.

6. A process according to claim 1, wherein the protein is initially dissolved in a bufffered aqueous solution whose pH is between about 7.5 and about 10.5.

7. A process according to claim 1, wherein a surfactant or emulsifying agent capable of forming a nanoemulsion is used in the emulsion step.

8. A process according to claim 1, wherein the emulsion is carried out by means of stirring with a shear effect, at a minimum of 20,000 rpm, or with a cavitation effect.

9. A process according to claim 1, wherein an emulsion of the oil phase and of the water phase is prepared as a first step and, as a second step, a nanoemulsion is produced by passing the emulsion through a homogenizer under a pressure of at least 400 bar.

10. A process according to claim 1, wherein the protein comprises collagen.

11. A process according to claim 1, wherein the protein comprises atelocollagen.

12. A process according to claim 1, wherein the protein is atelocollagen and is admixed with a glycosaminoglycan.

13. A process according to claim 1, wherein one of the phases contains a water-soluble, liposoluble or insoluble cosmetically, pharmaceutically or foodstuff active principle.

14. A process according to claim 13, wherein, when the active principle is water-soluble or insoluble, an oil/water emulsion ratio of about 6 is used.

15. A process according to claim 13, wherein, when the active principle is liposoluble, a water/oil emulsion ratio of about 20 is used.

16. A process according to claim 15, wherein a protein with a high molecular weight of at least 50,000 Daltons is used and the concentration of the protein is such that the viscosity of the aqueous phase containing said protein is below about 20 cp.

17. A nanocapsule or nanoparticle, which comprises a crosslinked protein wall which has been prepared by the process of claim 1.

18. A cosmetic, pharmaceutical or food composition which comprises nanocapsules or nanoparticles according to claim 17, containing a water-soluble, liposoluble or insoluble cosmetically, pharmaceutically or foodstuff active principle.

19. The process of claim 1, wherein said protein is selected from the group consisting of elastin, keratin, silk, albumin, a milk protein, collagen, atelocollagen, wheat, maize, oat, almond protein, a fish protein, an algae protein, a plankton protein and a micro-plankton protein.

20. A process according to claim 1, wherein the protein is in the water phase and the crosslinking agent is in the oil phase.

21. A process for the production of nanocapsules or nanoparticles, having a size less than 1 micron, said nanocapsules or nanoparticles having cross-linked protein-based walls, which process comprises preparing a nanoemulsion of said proteins comprising an oil phase and a water phase, defining an interface between said water phase and said oil phase either of a water-in-oil emulsion or of an oil-in-water emulsion and forming said nanocapsules or nanoparticles from said nanoemulsion, wherein an interfacial cross-linking reaction is carried out between said proteins and a cross-linking agent selected from the group consisting of an acid dichloride, an acid anhydride and a dibasic or polybasic carboxylic acid, so as to yield said nanocapsules or nanoparticles, with cross-linked protein-based walls.

22. A process according to claim 21, wherein the emulsion further comprises a viscosity modifier for diminishing the viscosity between the phases.

23. A process according to claim 22, wherein the viscosity modifier is capable of modifying the viscosity by a factor of at least 4, relative to the phase to which said modifier is added.

24. A process according to claim 22 wherein, a water-in-oil emulsion, is prepared and said viscosity modifier is added to or substituted for the oily phase so as to increase the viscosity by a factor of at least 4, relative to the viscosity of the oily phase used.

25. The process of claim 21, wherein said cross-linking agent is selected from the group consisting of terephthaloyl chloride, phthaloyl chloride, sebacoyl chloride, succinoyl chloride, citric acid chloride, and succinic anhydride.

26. Thee process of claim 21, wherein said protein is selected from the group consisting of an animal protein, a vegetable protein and a protein originating from a marine source.

27. The process of claim 21, wherein said protein is selected from the group consisting of elastin, keratin, silk, albumin, a milk protein, collagen, atelocollagen, wheat, maize, oat, almond protein, a fish protein, an algae protein, a plankton protein and a micro-plankton protein.

28. The process of claim 21, wherein the content of protein in the emulsion solution ranges between 0.1 and 5% by weight, based on the total weight of the emulsion.

29. The process of claim 21, wherein said proteins are initially dissolved in a buffered aqueous solution having a pH of between about 7.5 and about 10.5.

30. The process of claim 21, wherein the emulsion is prepared with the use of a surfactant or emulsifying agent capable of forming a nanoemulsion.

31. The process of claim 30, wherein said surfactant or emulsifying agent is glycerol sorbitan hydroxyisostearate.

32. The process of claim 21, wherein an emulsion of the water phase and of the oil phase is prepared in a first step and then said emulsion is passed through a homogenizer under a pressure of at least 400 bars to produce said nanoemulsion.

33. The process of claim 21, wherein said protein is atelocollagen and is admixed with a glycosaminoglycan.

34. The process of claim 21, wherein a protein with a high molecular weight of at least 50,000 Daltons is added to the water phase and the concentration of the protein in the water phase is such that the viscosity of the water phase obtained is below about 20 cp.

35. A process according to claim 22, wherein the viscosity modifier is selected from the group consisting of a viscous oil whose viscosity is at least 80 cp and a viscosity modifier for oils.

36. A process according to claim 35, containing liquid paraffin as the viscous oil.

37. A process according to claim 35, wherein the viscosity modifier is magnesium stearate.

38. Nanocapsules or nanoparticles having a size less than 1 micron, comprising a crosslinked outer wall having been obtained from a nanoemulsion by an interfacial crosslinking reaction between at least one protein having acylatable groups and a crosslinking agent having reactive groups capable of reacting with said acylatable groups of said protein to form interfacial crosslinking.

39. Nanocapsules or nanoparticles having a size less than 1 micron, comprising a crosslinked outer wall having been obtained from a nanoemulsion by an interfacial crosslinking reaction between at least one protein having acylatable groups and a crosslinking agent having reactive groups capable of reacting with said acylatable groups of said protein to form interfacial crosslinking wherein the crosslinking agent is selected from the group consisting of an acid dichloride, an acid anhydride, and a dibasic or polybasic carboxylic acid.

40. A product according to claim 38, wherein said crosslinking agent is selected from the group consisting of terephthaloyl chloride, phthaloyl chloride, sebacoyl chloride, succinoyl chloride, citric acid chloride, and succinic anhydride, and wherein said protein is selected from the group consisting of elastin, keratin, silk, albumin, a milk protein, collagen, atelocollagen, wheat maize, oat, almond protein, a fish protein, an algae protein, a plankton protein and a micro-plankton protein.

41. A product according to claim 39, wherein said nanocapsule comprises a mixture of atelocollagen and a glycosaminoglycan.

42. Nanocapsules or nanoparticles having a size less than 1 micron, comprising a crosslinked outer wall surrounding an innerspace, said crosslinked outer wall having been obtained from a nanoemulsion by an interfacial crosslinking reaction between at least one protein and a crosslinking agent, wherein said protein is selected from the group consisting of elastin, keratin, silk, albumin, a milk protein, collagen, atelocollagen, wheat, maize, oat, almond protein, a fish protein, an algae protein, a plankton protein and a micro-plankton protein, and said crosslinking agent is an acid dichloride, an acid anhydride, or a dibasic or polybasic carboxylic acid.

43. A product according to claim 42, wherein said nanocapsule comprises a mixture of atelocollagen and glycosaminoglycan.

44. A product according to claim 38, having a rate of release of active substance slower than a micro capsule having the same chemical constituents.

45. A product according to claim 42, having a rate of release of active substance slower than a micro capsule having the same chemical constituents.

46. A process for the production of nanocapsules or nanoparticles having a size less than 1 micron, said nanocapsules or nanoparticles having crosslinked protein-based walls, which process comprises preparing a water-in-oil nanoemulsion of at least one acylatable group-containing protein in water phase dispersed in an oily phase containing a crosslinking agent having reactive groups capable of reacting with said acylatable groups of said protein, and at least one viscosity modifier for diminishing the difference in viscosity between said phases, defining an interface between said dispersed water phase and said oily phase, and forming said nanocapsules or nanoparticles from said nanoemulsion by performing an interfacial crosslinking reaction between said acylatable groups of said protein and said reactive groups of said crosslinking agent at said interface so as to yield said nanocapsules or nanoparticles with crosslinked protein-walls and having said size.

47. A process for the production of nanocapsules or nanoparticles, having a size less than 1 micron, said nanocapsules or nanoparticles having crosslinked protein-based walls, which process comprises preparing an oil-in-water nanoemulsion, said nanoemulsion comprising at least one acylatable group-containing protein in a water phase and dispersed therein an oily phase containing a crosslinking agent having reactive groups capable of reacting with said acylatable groups of said protein, defining an interface between said water phase and said dispersed oily phase, said nanoemulsion being obtained by dispersing said oily phase in said water phase by means of a shearing with a shear effect at a minimum of 20,000 rpm, and forming said nanocapsules or nanoparticles from said nanoemulsion by an interfacial crosslinking reaction between said acylatable groups of said protein and said reactive groups of said crosslinking agent at said interface as to yield said nanocapsules or nanoparticles with crosslinked protein-based walls and having said size.

48. A process for the production of nanocapsules or nanoparticles, having a size less than 1 micron, said nanocapsules or nanoparticles having crosslinked protein-based walls, which process comprises preparing an oil-in-water nanoemulsion, said emulsion comprising at least one acylatable group-containing protein in a water phase and dispersed therein an oily phase containing a crosslinking agent having reactive groups capable of reacting with said protein, defining an interface between said water phase and said dispersed oily phase, said nanoemulsion being obtained by dispersing said oily phase in said water phase and passing the admixture of the dispersed oily phase and water phase one or more times through a high pressure homogenizer working at a pressure of at least 400 bars, and forming said nanocapsules or nanoparticles from said nanoemulsion by an interfacial crosslinking reaction between said acylatable groups of said protein and said reactive groups of said crosslinking agent at said interface so as to yield said nanocapsules or nanoparticles with crosslinked protein-based walls.

49. A process for the production of nanocapsules or nanoparticles, having a size between about 100 to 800 nanometers, said nanocapsules or nanoparticles having crosslinked protein-based walls, which process comprises preparing a nanoemulsion of at least one acylatable group-containing protein, said emulsion comprising a water phase, an oil phase, defining an interface between said water phase and said oil phase either of a water-in-oil emulsion or an oil-in-water emulsion, and forming said nanocapsules or nanoparticles from said nanoemulsion, wherein an interfacial crosslinking reaction is carried out, between said protein and a crosslinking agent having reactive groups capable of reacting at said interface with said acylatable groups of said protein, so as to yield said nanocapsules or nanoparticles with crosslinked protein-based walls.

50. A process for the production of nanocapsules or nanoparticles, having a size between about 100 to 800 nanometers, said nanocapsules or nanoparticles having cross-linked protein-based walls, which process comprises preparing a nanoemulsion of said proteins comprising an oil phase and a water phase, defining an interface between said water phase and said oil phase either of a water-in-oil emulsion or of an oil-in-water emulsion and forming said nanocapsules or nanoparticles from said nanoemulsion, wherein an interfacial cross-linking reaction is carried out between said proteins and a cross-linking agent selected from the group consisting of an acid dichloride, an acid anhydride and a dibasic or polybasic carboxylic acid, so as to yield said nanocapsules or nanoparticles, with cross-linked protein-based walls.

51. Nanocapsules or nanoparticles, having a size between about 100 to 800 nanometers, comprising a crosslinked outer wall having been obtained from a nanoemulsion by an interfacial crosslinking reaction between at least one protein having acylatable groups and a crosslinking agent having reactive groups capable of reacting with said acylatable groups of said protein to form interfacial crosslinking.

52. Nanocapsules or nanoparticles, having a size between about 100 to 800 nanometers, comprising a crosslinked outer wall surrounding an innerspace, said crosslinked outer wall having been obtained from a nanoemulsion by an interfacial crosslinking reaction between at least one protein and a crosslinking agent, wherein said protein is selected from the group consisting of elastin, keratin, silk, albumin, a milk protein, collagen, atelocollagen, wheat, maize, oat, almond protein, a fish protein, an algae protein, a plankton protein and a micro-plankton protein, and said crosslinking agent is an acid dichloride, an acid anhydride, or a dibasic or polybasic carboxylic acid.

53. A process for the production of nanocapsules or nanoparticles having a size between about 100 to 800 nanometers, said nanocapsules or nanoparticles having crosslinked protein-based walls, which process comprises preparing a water-in-oil nanoemulsion of at least one acylatable group-containing protein in water phase dispersed in an oily phase containing a crosslinking agent having reactive groups capable of reacting with said acylatable groups of said protein, and at least one viscosity modifier for diminishing the difference in viscosity between said phases, defining an interface between said dispersed water phase and said oily phase, and forming said nanocapsules or nanoparticles from said nanoemulsion by performing an interfacial crosslinking reaction between said acylatable groups of said protein and said reactive groups of said crosslinking agent at said interface so as to yield said nanocapsules or nanoparticles with crosslinked protein-walls and having said size.

54. A process for the production of nanocapsules or nanoparticles, having a size between about 100 to 800 nanometers, said nanocapsules or nanoparticles having crosslinked protein-based walls, which process comprises preparing an oil-in-water nanoemulsion, said nanoemulsion comprising at least one acylatable group-containing protein in a water phase and dispersed therein an oily phase containing a crosslinking agent having reactive groups capable of reacting with said acylatable groups of said protein, defining an interface between said water phase and said dispersed oily phase, said nanoemulsion being obtained by dispersing said oily phase in said water phase by means of a shearing with a shear effect at a minimum of 20,000 rpm, and forming said nanocapsules or nanoparticles from said nanoemulsion by an interfacial crosslinking reaction between said acylatable groups of said protein and said reactive groups of said crosslinking agent at said interface so as to yield said nanocapsules or nanoparticles with crosslinked protein-based walls and having said size.

55. A process for the production of nanocapsules or nanoparticles, having a size between about 100 to 800 nanometers, said nanocapsules or nanoparticles having crosslinked protein-based walls, which process comprises preparing an oil-in-water nanoemulsion, said emulsion comprising at least one acylatable group-containing protein in a water phase and dispersed therein an oily phase containing a crosslinking agent having reactive groups capable of reacting with said protein, defining an interface between said water phase and said dispersed oily phase, said nanoemulsion being obtained by dispersing said oily phase in said water phase and passing the admixture of the dispersed oily phase and water phase one or more times through a high pressure homogenizer working at a pressure of at least 400 bars, and forming said nanocapsules or nanoparticles from said nanoemulsion by an interfacial crosslinking reaction between said acylatable groups of said protein and said reactive groups of said crosslinking agent at said interface so as to yield said nanocapsules or nanoparticles with crosslinked protein-based walls.

\* \* \* \* \*